US006001643A

United States Patent [19]
Spaulding

[11] Patent Number: 6,001,643
[45] Date of Patent: Dec. 14, 1999

[54] CONTROLLED HYDRODYNAMIC CELL CULTURE ENVIRONMENT FOR THREE DIMENSIONAL TISSUE GROWTH

[75] Inventor: Glenn F. Spaulding, Houston, Tex.

[73] Assignee: C-Med Inc., Houston, Tex.

[21] Appl. No.: 09/083,515

[22] Filed: May 22, 1998

Related U.S. Application Data

[60] Provisional application No. 60/054,657, Aug. 4, 1997.

[51] Int. Cl.[6] ................................................. C12M 3/02
[52] U.S. Cl. ................................. 435/298.2; 435/304.2; 435/288.2; 435/394
[58] Field of Search ............................. 435/394, 298.2, 435/304.1, 304.2, 288.2; 215/6; 366/220

[56] References Cited

U.S. PATENT DOCUMENTS

| | | | |
|---|---|---|---|
| 2,787,268 | 4/1957 | Greenspan | 215/6 |
| 3,521,745 | 7/1970 | Schwartzman | 215/6 |
| 3,750,645 | 8/1973 | Bennet et al. | 600/573 |
| 3,821,087 | 6/1974 | Rnazek et al. | 195/127 |
| 3,847,749 | 11/1974 | Smith et al. | |
| 3,918,909 | 11/1975 | Arlman | 422/71 |
| 4,391,912 | 7/1983 | Yoshida et al. | 435/400 |
| 4,749,654 | 6/1988 | Karrer et al. | 435/240.25 |
| 4,948,728 | 8/1990 | Stephanopauous et al. | 435/41 |
| 4,962,033 | 10/1990 | Serkes et al. | 435/395 |
| 5,010,013 | 4/1991 | Serkes et al. | 435/299.2 |
| 5,015,585 | 5/1991 | Robinson | 435/401 |
| 5,026,650 | 6/1991 | Schwarz et al. | 435/286 |
| 5,057,428 | 10/1991 | Mizutani | 435/293.2 |
| 5,153,131 | 10/1992 | Wolf et al. | 435/345 |
| 5,330,908 | 7/1994 | Spaulding | 435/240.24 |
| 5,437,998 | 8/1995 | Schwarz et al. | 435/298.2 |
| 5,449,617 | 9/1995 | Falkenberg et al. | 435/394 |
| 5,496,722 | 3/1996 | Goodwin et al. | 435/240.23 |
| 5,523,228 | 6/1996 | Ingram et tal. | 435/394 |
| 5,527,705 | 6/1996 | Gray | 435/297.1 |
| 5,567,598 | 10/1996 | Stitt et al. | 435/29 |
| 5,589,112 | 12/1996 | Spaulding | 264/413 |
| 5,637,477 | 6/1997 | Spaulding et al. | 435/69.1 |
| 5,665,594 | 9/1997 | Schwarz et al. | 435/394 |
| 5,763,279 | 6/1998 | Schwarz et al. | 435/383 |

OTHER PUBLICATIONS

Dedolph et al.'The physical basis of gravity stimulus nullification by clinostat rotation.' Plant Physiology. vol. 47 (1971), pp. 756–764.
Lewis et al.'Growth and maintenance of anchorage dependent cells in zero headspace bioreactor systems designed for microgravity.' Proceedings, Spacebound '87. May 1987.
Peterson et al. 'Fiber Optic pH probe for physiological use.' Anal. Chem. Vol. 52 (1980), pp. 864–869.
Peterson et al.'Fiber–Optic probe for in Vivo measurement of oxygen partial pressure.' Anal. Chem. vol. 56 (1984), pp. 62–67.
Towe et al. 'A recirculating–flow fluorescent oxygen sensor.' Biosen. Bioelect. vol. 11 (1996), pp. 799–803.
Spaulding. 'Perfusion in a NASA cell culture system.' In–Vitro, 30A(3), Pt. 2:52–53(1994). Abstract only.
Aunins, J.G.,et al. 'Engineering Developments in Homogeneous Culture of Animal Cells: Oxygenation of Reactors and Scale–up.' Biotechnology and Bioengineering Symp, N. 17,699–723, 1986.

Primary Examiner—William H. Beisner

[57] ABSTRACT

A novel hydrodynamic cell culture environment is disclosed for a two-chamber roller bottle. The unstable hydrodynamics of a gas headspace media chamber is coupled through a center opening to a second zero headspace culture chamber. Coupling the two chambers creates novel fluid streamlines that add turbulence for improved mass transfer and slow media repletion. The exchange between chambers regulates turbulence and thus concomitant exchange of nutrients i.e., environmental control. It is disposable, automatable, and suited to culturing tissue for transplants.

5 Claims, 2 Drawing Sheets

CONTROLLED HYDRODYNAMIC CELL CULTURE ENVIRONMENT FOR THREE DIMENSIONAL TISSUE GROWTH

This application claims the benefit of U.S. Provisional Application No. 60/054,657, filed Aug. 4, 1997.

FIELD OF THE INVENTION

The present invention relates a novel hydrodynamic cell culture environment embodied in a two chamber roller bottle with a controlled environment and uniquely combines; turbulence, wall shear, gas-to-liquid mass transfer, and cell culture environmental control, to the engineering of tissue constructs. Environmental parameters are aseptic and controlled, therein engineering the outcome of the tissue construct. The invention herein disclosed is especially suited to the culture of autologous tissues for clinical transplants, methods for engineering tissue constructs; and the product from the process. Tissue constructs derived from the novel hydrodynamic culture environment of this invention are phenotypically different from tissue constructs obtained by other culture vessels.

BACKGROUND OF THE INVENTION

The culture process for mammalian cells, animal cells, insect cells, bacteria, yeast and molds has one major rate-limiting step, oxygen mass transfer. Oxygen metabolism is essential for metabolic function. In mammalian and animal cell culture, oxygen flux is especially important during the early stages of rapid cell division. Oxygen utilization per cell is greatest when cells are suspended; requirements decrease as the cells aggregate and differentiate. However, during the later phases of cell culture, as the number of cells per unit volume increases, the bulk oxygen mass transfer requirements increase. Traditionally, increased requirements are accommodated by mechanical stirring methods. The present invention integrates several features needed for the engineering of autologous tissue transplants. Incorporated into the invention are; automated cell culture media repletion, the capability to grow cells in monolayer, a turbulent hydrodynamic cell culture environment suited to the growth of three-dimensional tissue constructs, a unique configuration that allows both monolayer and 3-dimensional culture in a variety of combinations, a gas head space for direct oxygenation of the cell culture media, an internal sensor for aseptically monitoring media changes, the capability to aseptically regulate both media repletion and add turbulence for improved mass transfer, and all features are included in a very low cost disposable two chamber tissue culture roller bottle. It will be appreciated by those of ordinary skill in the art, that the invention eliminates a large portion of the cell culture labor costs. The instant invention; 1) establishes near physiological control for improved engineering of tissue constructs, 2) enhances mass transfer through hydrodynamic shear forces generated at the wall and through the turbulent interface with the first chamber, 3) eliminates cellular contact with a potentially toxic silicone membrane oxygenator because oxygenation is predominately through the air fluid interface, 4) increases the concentration of de novo growth factors because the media is not replaced as often, and 5) greatly reduces the risk of contamination.

Culturing tissue for transplantation requires that several conditions be met before the tissue receives Food and Drug Administration (FDA) approval. Those FDA conditions include; functionality that ameliorates the disease; consistent and reproducible growth of tissue constructs; and proven sterility. To achieve in vivo functionality, engineered tissue constructs must be three-dimensional. To be reproducible, the cell culture environment should be regulated to match human physiology, a feature of the invention. Data from the aseptic monitoring of the growing construct can be used to validate sterility and establish specifications.

Transplantable tissue has three key features; 1) an extracellular matrix for mechanical stability and scaffolding; 2) cell-to-cell contact to maintain viability and function; and 3) a three-dimensional shape to segregate cell subpopulations for growth and proliferation. Standard tissue culture approaches (e.g.; t-flasks, petri dishes, microgravity culture vessels, roller bottles and stirred roller bottles) have consistently failed to yield transplantable tissue that directly supplants organ function. Failure is often related to the loss of multi-dimensional cell-to-cell contacts and the overgrowth of unwanted cell subpopulation. In roller bottles and stirred reactors, cells are prevented from sustained three-dimensional growth. Shear preselects for only those cell subpopulations that are robust to its damage. The present invention controls the addition of turbulence and concomitant shear, and localizes shear to specific areas. There are other selection pressures that impede normal growth, besides those intrinsic to standard cell culture roller bottles. Specifically, those technical operations associated with feeding the culture. Standard cell culture practice replaces cell culture media at regular intervals or when the media changes color. Replacing the media at regular intervals dilutes growth factors that are vital to cell growth and proliferation, and typically exposes cells to abnormally high oxygen concentrations. Abnormally high oxygen exposure occurs when spent cell media is replaced with fresh media. Fresh media equilibrated to room air has a dissolved oxygen concentration of approximately 159 mm Hg, often more than double the normal concentration found in the average mammalian interstitial space (normal 40–80 mm Hg). High levels of oxygen are known to be toxic to highly differentiated cells. Therefore, the practice of replacing conditioned media with fresh media equilibrated to ambient air, preselects for cells that are less sensitive to oxygen toxicity (e.g.; fibroblasts). Changing media based on the pH indicator dye, phenol red, imposes another common environmental selection pressure. Human physiology maintains the vascular and interstitial pH between 7.30–7.40. Deviation beyond physiological limits often results in mental confusion and organ dysfunction. Yet, most cell culture facilities routinely maintain the pH within 7.00 to 7.45. If patients were repeatedly exposed to standard cell culture pH extremes, they would eventually succumb to multi-system organ failure.

There are several deficiencies associated with continuous perfusion of cell cultures. Continuous perfusion consumes large amounts of cell culture media, serum, and growth factor supplements. The expenses associated with perfusion reactors preclude their general use in research, and perfusion often yields tissue constructs that are delicate and of poor functionality. There are several additional drawbacks to profusion culture; cell populations are first manually expanded as monolayers of cells, yielding an atypical architecture; subpopulations that are robust and grow rapidly, overgrowing the other populations; and the cells must be anchorage dependant to keep from being washed away in the perfusion stream.

A three-dimensional architecture is required for tissue constructs to be functional. As aggregates of cells organize, they exhibit the architecture of nascent tissue. To create a tissue construct, dissimilar cell types must aggregate, free from the selection pressures that force cells to spread and grow along a flat surface. Hydrogels and media viscosity enhancers permit cell mixtures to remain in contact with other cells, thereby allowing three-dimensional tissue growth. However, it has been observed that the sizes of the constructs were small, and latter deduced that they were mass transfer limited.

Roller bottles are ubiquitous to cell culture facilities, and have been in use for decades. Their strengths are; they are disposable and offer a large surface for cell attachment. Their weakness is a consequence of the large uncontrolled hydrodynamic shear associated with a gas headspace and the abundance of turbulent eddies. The high shear environment inherent in roller bottles precludes their use for growing tissue for transplantation. Only those cell types that are not damaged by the shear and adhered to the wall, can be maintained in culture for the extended periods.

Horizontal rotation for suspension i.e., clinostatic rotation, began in the 1700s. The physics for growing cells in a free fall or in a microgravity like environment, was first characterized in detail by the Argonne National Laboratory (R. R. Dedolph and M. H. Dipert, 1971). Those principles were applied in the NASA microgravity culture vessels and cell culture methods, and the vessel and culture methods were first disclosed by M. Lewis et. al., May 1987. Later, the tubular silicone oxygenator in the culture vessel of M. Lewis et. al., 1987, was replaced by a membrane silicone oxygenator, and the culture vessel patented by NASA—U.S. Pat. No. 5,026,650 issued June 1991. Culture systems developed by NASA strive to achieve a quiescent microgravity like environment, having origins in the NASA space program. Microgravity culture conditions are created by low shear and essentially no relative motion of the culture environment with respect to the walls of the culture vessel (U.S. Pat. No. 5,496,722; claim 12). Essentially no relative motion differences between the culture media and the vessel wall, is often referred to as solid body rotation. The forces maintaining solid body rotation are associated with the 1:1 viscous coupling between the vessel wall and the cell culture media contained in the vessel (G. F. Spaulding, 1994). However, microgravity is known to cause aberrancy. There are over 100 scientific articles and abstracts demonstrating or suggesting microgravity induced aberrancy in cell growth, cell differentiation, cell movement, cell size and shape, cell physiology, apoptosis, abnormal cell cycle, abnormal phenotypes, or general human physiology, occurring in rotating culture systems or in actual microgravity. The normal mammalian hydrodynamic milieu differs from a quiescent microgravity like environment. In utero, cells are constantly moved, pulled or forced to settle in different directions depending on the position of the organism, i.e.; standing, sitting or lying down. Movements from walking, running, and breathing agitate the cells; thereby adding hydrodynamic shear. An intrauterine environment is characterized by cells developing in amniotic fluid under constant hydrodynamic shear, resulting in high mass transfer. The present invention more closely emulates the intrauterine hydrodynamic and gas mass transfer environment where positional changes, breathing, movement, and hemodynamic pulsations continuously disrupt boundary layers. At the same time, the maternal physiology closely regulates the intrauterine environment; facilitating normal growth of organs. Major changes in maternal physiology would elicit great concern for abnormal fetal organ development. Yet, the standard of tissue culture practice for those of ordinary skill in the art, is to allow the cell culture pH and oxygen to fluctuate beyond in vivo limits.

The invention, herein disclosed, integrates a novel hydrodynamic cell suspension environment, with regulation of media repletion and pulsatile mass transfer or diffusive, to achieve three-dimensional tissue constructs suitable for transplantation. An automated tissue culture system that facilitates three-dimensional growth, and is disposable, fulfills a need for technology to engineer autologous tissue constructs, as well as grow cells for basic research.

PRIOR ART

Publications

M. L. Lewis, et. al., "Growth and Maintenance of Anchorage Dependent Cells in Zero Headspace Bioreactor Systems Designed for Microgravity", Proceedings, Spacebound '87, First Canadian Workshop on R&D Opportunities on Board the Space Station, May 6–8, 1987.

"Space Bioreactor Science Workshop" Proceedings of an August, 1985 workshop by NASA, ED: D. R. Morrison, Government publication: NASA Conference Publication 2485, December, 1987.

Aunins, J. G., M. S. Croughan, D. I. C. J. Wang, and J. M. Goldstein, Engineering Developments in Homogeneous Culture of Animal Cells: Oxygenation of Reactors and Scale-up, Biotechnology and Bioengineering Symp, No. 17, 699–723, 1986.

Spaulding, G. F., "Perfusion in a NASA Cell Culture System", In-Vitro, 30A(3), Pt.2:52–53, 1994.

Towe, B. C., Flechsig, S., and G. Spaulding (1996) A Recirculating-Flow Fluorescent Oxygen Sensor, Biosensors & Bioelectronics, 11(8):799–803.

Peterson, J. I., R. V. Fitzgerald, D. K. Buckhold (1984) Fiber-Optic Probe for in Vivo Measurement of Oxygen Partial Pressure, Anal. Chem., 56:62–67.

Peterson, J. I., Goldstein, S. R., and R. V. Fitzgerald (1980) Fiber Optic pH Probe for Physiological Use, Anal. Chem. 52:864–869.

Prior art includes the following patents and, the references cited therein, and are also incorporated herein fully as if set out verbatim.

U.S. Pat. No. 5,527,705 issued to E. F. Mussi and H. E. Gray on Jun. 18, 1996, is an example of a two chamber roller bottle. The chambers are coaxially aligned and separated by a microporous structure for the physical separation of two cell populations, one in each chamber. Both chambers have a gas headspace and are coaxially aligned. In contrast, the present invention has a zero headspace cell culture chamber in communication with a second chamber having a gas headspace, and a partition segments the roller bottle into two cylindrical chambers. The two chambers are contiguous through a hole in the center of the partition.

U.S. Pat. No. 5,010,013 issued to J. M. Serkes et. al., on Apr. 23, 1991, is an example of a cell culture roller bottle with increased surface area for cell attachment. Corrugated channels were designed to add interior surface area for cellular attachment. The roller bottle teaches against cell suspension. It is of signal chamber design with a gas head space.

U.S. Pat. No. 5,449,617 issued to F. W. Falkenberg, et. al., Sep. 12, 1995, relates to a roller bottle with a dialysis membrane separating two chambers. Both chambers have a gas headspace. The separating membrane is impermeable to liquids and microorganisms. In contrast, the present invention has a zero headspace cell culture chamber in communication with a second chamber having a gas headspace, and a partition segments the roller bottle into two cylindrical compartments—both chambers are hydrodynamically coupled.

U.S. Pat. No. 3,847,749 issued to R. E. Smith, et. al., Nov. 12, 1974, relates to the automation of roller bottle feeding. Control elements are external to the roller bottle. In contrast, the present invention has internal control elements.

U.S. Pat. No. 5,523,228 issued to M. Ingram, G. F. Spaulding, et. al., Jun. 4, 1996, relates to a single chamber zero headspace gas permeable horizontally rotating cell culture bag. The bag is compliant. Oxygenation is through an air-membrane-fluid interface, and therefore gas mass transfer is substantially governed by the thickness and the diffusivity coefficient of the membrane oxygenator (J. G. Aunins, et.al., 1986); and boundary layer gradients. In contrast, the present invention has a zero headspace cell culture chamber in communication with a second chamber having a gas headspace, and a partition segments the roller bottle into two cylindrical compartments—both chambers are hydrodynamically coupled.

U.S. Pat. Nos. 5,589,112 and 5,330,908 issued to G. F. Spaulding, and U.S. Pat. Nos. 5,026,650, 5,153,131, 5,437,998 and 5,665,594 relate to a gas permeable horizontally rotating microgravity cell culture vessels with zero headspace and solid body rotation. Solid-body horizontal rotation with zero headspace establishes a 1:1 viscous coupling of the culture media with the vessel wall, thereby eliminating boundary layers of gradient hydrodynamic shear (G. F. Spaulding, In-Vitro, 1994, 30A(3),Pt.2:52–53). Oxygenation is through an air-to-membrane-to-fluid interface, and therefore gas mass transfer is substantially governed by the thickness and the diffusivity coefficient of the membrane oxygenator; and boundary layer gradients (J. G. Aunins, et.al., 1986). They teach against turbulence. In contrast, the present invention teaches turbulence, teaches hydrodynamic gradients, teaches tangential cell motion with media exchange, teaches oxygenation by direct contact of the gas with the media, and teaches a gas headspace.

U.S. Pat. No. 5,057,428 issued to S. Mizutani et. al. on Oct. 15, 1991, relates to a cylindrical bioreactor tank which is rotated about a horizontal axis. There is a cylindrically shaped mesh in the chamber, which defines inner and outer chambers. Pipes conveys oxygen from an air pump into the chamber and a flow path is established to flow return pipes which provide for continuous replenishment of spent media. It is complicated to assemble and disassemble.

U.S. Pat. No. 5,015,585 issued to J. R. Robinson, on May 14, 1991, discloses a bioreactor construction utilizing a single polymer in a concentric geometric configuration to add durability and reduce complexity.

U.S. Pat. No. 3,821,087 issued to R. A. Rnazek et. al., on Jun. 28, 1974, discloses a cell growth system where cells are grown on membranes in a nutrient medium. Nutrient fluids carrying oxygen flow through the roller bottle and pass through a membrane to contact the cell culture. The fluid is driven by an impeller into the culture roller bottle. Numerous capillaries are used to distribute oxygen and nutrients over a large area to reduce uneven distribution of resources. There is no rotation of the roller bottle. It is complicated to assemble and disassemble.

U.S. Pat. No. 4,749,654 issued to D. Karrer et. al., on Jun. 7, 1988, relates to a cell growth system using gas permeable membranes and a waste gas removal system. A stirrer is used for agitation. Oxygen flows in through one side of the membrane and carbon dioxide flows out the other.

U.S. Pat. No. 4,948,728 issued to G. Stephanopauous et. al., on Aug. 14, 1990, discloses a porous ceramic material with a plurality of flow passages. A biofilm is in contact with an inner wall and a gas permeable membrane covers the outer wall. An oxygen flow along the outer wall permeates the membrane and ceramic housing to reach the biomaterial. Nutrients flow along the inner wall in direct contact with the biofilm. There is no rotation of the roller bottle.

U.S. Pat. No. 4,962,033 issued to J. M. Serkes et. al., on Oct. 9, 1990, is an example of a cell culture roller bottle with increased surface area for cell attachment. Corrugated channels were designed to add interior surface area for cellular attachment. In contrast to the present invention in which there is a zero headspace cell culture chamber in communication with a media containing chamber that has a gas headspace; the roller bottle has a single compartment with a gas headspace. The roller bottle teaches against cell suspension.

U.S. Pat. No. 4,391,912 issued to K. Yoshida et. al., on Jul. 5, 1983, is an example of a cell culture system with hollow fibers that is not rotated.

U.S. Pat. No. 5,496,722 and 5,637,477 issued to G. F. Spaulding et. al., relate to culturing in NASA microgravity culture vessels in solid-body rotation with zero headspace. Solid-body horizontal rotation with zero headspace establishes a 1:1 viscous coupling of the culture media with the vessel wall, thereby eliminating boundary layers of gradient hydrodynamic shear (G. F. Spaulding, In-Vitro, 1994, 30A (3),Pt.2:52–53). Oxygenation is through an air-to-membrane-to-fluid interface, and therefore gas mass transfer is substantially governed by the thickness and the diffusivity coefficient of the membrane oxygenator; and boundary layer gradients (J. G. Aunins, et.al., 1986). We did not maintain a physiological pH. We taught against turbulence. In contrast, the present invention teaches turbulence, teaches hydrodynamic gradients, teaches tangential cell motion with media exchange, teaches oxygenation by direct contact of the gas with the media, and teaches a gas headspace. The novel hydrodynamics and novel culture environment yields cellular constructs with unique phenotypes.

U.S. Pat. No. 5,567,598 issued to D. T. Stitt et. al., on Oct. 22, 1996, discloses the use of ruthenium diimine complexes for the detection and evaluation of metabolic activity of microorganisms based on their ability to consume dissolved oxygen. A ruthenium diimine complex was used in a t-flask to measure *E. coli* growth. They did not teach monitoring of tissue metabolism, the sensor and instrument adaptations required for monitoring a sensor in rotation were not taught, and they did not teach oxygen regulation based on sensor data. The current invention improves the prior art by adapting a ruthenium diimine complex based sensor and monitoring instruments to a rotating culture vessel, and utilizes the adaptation for monitoring and controlling dissolved oxygen.

Towe, B. C., Flechsig, S., and G. Spaulding (1996) A Recirculating-Flow Fluorescent Oxygen Sensor, Biosensors & Bioelectronics, 11(8):799–803. We disclosed the characteristics of a liquid ruthenium diimine mixture for dissolved oxygen sensing. We taught against solid phase sensors.

Peterson, J. I., R. V. Fitzgerald, D. K. Buckhold (1984) Fiber-Optic Probe for in Vivo Measurement of Oxygen Partial Pressure, Anal. Chem., 56:62–67. They teach optical sensing of oxygen. They did not teach monitoring of tissue culture metabolism, the sensor and instrument adaptations required for monitoring a sensor in rotation were not taught, and they did not teach oxygen regulation based on sensor data Peterson, J. I., Goldstein, S. R., and R. V. Fitzgerald (1980) Fiber Optic pH Probe for Physiological Use, Anal. Chem. 52:864–869. They teach optical sensing of pH and the use of phenol red. They did not teach monitoring of tissue culture metabolism, the sensor and instrument adaptations required for monitoring a sensor in rotation were not taught, and they did not teach pH regulation based on sensor data

SUMMARY OF THE PRESENT INVENTION

In the present invention, the culture vessel is embodied in a roller bottle having an open first end and an enclosed second end. The open first end is used to introducing and remove media and is large. Said large opening enables the removal of large tissue constructs—in contrast to t-flasks and syringe ports. A means for retaining the culture media is disposed to said first end. Said mean for media retention is disposed to said first end to form a substantially fluid tight seal. Said means for retaining culture media can be a commercially obtained cap, as is know in the art. The roller bottle is partitioned into two chambers, a first chamber and a second chamber. Said first chamber is the media chamber; and is defined by said first end with means for media retention, and a partition. Said second chamber is the tissue culture chamber; and is defined by said partition and said enclosed second end. Both first and second chambers are contiguous through an opening in said partition. Said opening in said partition is centered with the central annular axis of the roller bottle. Said opening in said partition is smaller than the inner diameter of the roller bottle, i.e.; the area of the opening is less than the area the partition subtends in the roller bottle.

In constructing the roller bottle, the roller bottle is constructed of materials that are suitable for cell and tissue culture. Said materials are known in the art and can be chosen from; polystyrene, glass, polyethylene, polysulfone, methyl methacrylate, high density polyethylene, low density polyethylene, polyethylene terephthalate glycol, perfluoroalkoxy, polycarbonate, polyvinylidene fluoride, polytetrafluoroethylene, ultra high molecular weight polyethylene, nylon, Teflon®, crystalline polystyrene, metallocene-based polypropylenes, syndiotatic polystyrene, and the like. In one embodiment, said roller bottle is constructed as a single unit, by injection molding or blow molding or extrusion, out of crystalline polystyrene, said walls defining said roller bottle being substantially impermeable to gas and liquid exclusive of said opening in said partition. In an alternate embodiment, said roller bottle is the assemblage of two members. A first cylinder member having an open first end and an enclosed second end; and, a second cylinder member having an open first end and an enclosed second end. Said second end of said second cylinder member defines said partition. Said second cylinder member is inserted into said first cylinder member whereby said partition and said enclosed second end of said first cylinder member defines the second chamber (tissue culture chamber). Said second cylinder member and cap means for retaining fluid defines said first chamber (media chamber). Said cap means is disposed to said first cylinder member in a fashion to secure said second cylinder member within said first member and retain media.

In constructing said means for retaining media, the fluid retention means is constructed of materials that are suitable for cell and tissue culture. Said materials are known in the art, and can be chosen from: polystyrene, glass, polyethylene, polysulfone, methyl methacrylate, high density polyethylene, low density polyethylene, polyethylene terephthalate glycol, perfluoroalkoxy, polycarbonate, polyvinylidene fluoride, polytetrafluoroethylene, ultra high molecular weight polyethylene, nylon, Teflon®, crystalline polystyrene, metallocene-based polypropylenes, syndiotatic polystyrene, and the like. In one embodiment, said fluid retention means is a cap constructed of optically transparent crystalline polystyrene, and secured to the roller bottle by screw threads therein forming a substantially fluid tight seal. Said roller bottle having a closed environment substantially free from gas exchange.

In a alternate embodiment for an open environment for gas exchange, said cap is comprised of microporous polymeric materials with high liquid intrusion pressures (e.g., Pall Specialty Materials, N.Y.). Said microporous materials enables enhanced gas exchange between the gas headspace in the first chamber and the ambient external air. Said gas exchange would be of higher flux, with respect to gas-to-membrane-to-fluid exchange, because it is known in the art that gas-to-membrane-to-gas exchange has a higher rate of transfer because of the lower solubility of gas in liquid. Therefore, gas exchange through a liquid-membrane-liquid process is slower than a gas-membrane-gas process. Herein disclosed as a novel means for oxygen transfer to a gas headspace chamber. Oxygenation from ambient air-to-membrane-to-gas headspace then from gas headspace-to-media from said first chamber to said second chamber provides for greater gas mass transfer—a novel gas mass transfer process. Suitable microporous materials are known in the art and are commercially available in a variety of sizes and materials. Materials for microporous cap construction can be chosen from: polystyrene, glass, polyethylene, polysulfone, methyl methacrylate, high density polyethylene, low density polyethylene, polyethylene terephthalate glycol, perfluoroalkoxy, polycarbonate, polyvinylidene fluoride, polytetrafluoroethylene, ultra high molecular weight polyethylene, nylon, Teflon®, crystalline polystyrene, metallocene-based polypropylenes, syndiotatic polystyrene, and the like.

In the alternate embodiment, microporous materials can include microporous membranes that are known in the art and are commercially available as screw on caps having a microporous membrane disposed to the cap that allows gas exchange yet retains fluid. In the art there are two problems with gas exchange membranes that are in direct contact with a zero headspace culture chambers. 1) A cell coming in direct contact with a gas exchange membrane may become toxic because of the high oxygen concentration at the interface; 2) The materials used to construct the membrane are often toxic; and 3) When there is a gas headspace on one side of a gas exchange membrane, and media having zero head space on the other side, media is lost by evaporation. Media evaporating from the zero headspace side to the gas headspace side, lowers the pressure on the media side. Eventually, when the pressure is low enough, gas is drawn from the gas headspace side through the membrane to the media side, where the gas forms micro-bubbles at the membrane-fluid interface. With continued vapor loss, micro-bubbles can become larger and dislodge from the membrane, coalescing at the top of the culture chamber, therein causing increased shear in a horizontally rotating culture vessel. The invention herein disclosed, overcomes the prior art difficulties by establishing a novel gradient that favors bubble dissolution in the cell culture chamber (zero headspace, said second chamber).

In culturing tissue, the culture roller bottle is sterilized and fresh culture media, cells and/or tissue are admitted to completely fill the tissue culture chamber (said second chamber) without any bubbles, i.e.; zero headspace. Culture media without cells or tissue is admitted to the media chamber to fill approximately ⅔ of the media chamber volume (said first chamber). The remainder of the media chamber is filled with gas. A cap or other means to retain media is disposed to the roller bottle. The roller bottle is placed in a horizontal position. In placing the roller bottle in a horizontal position, the gas bubble in the media chamber becomes trapped at the top half of the media chamber (said first chamber) and above said opening in said partition. The gas volume is chosen so that the bubble is not so large as to move through said opening in said partition and enter said tissue culture chamber (said second chamber). A zero headspace second chamber and gas headspace first chamber establishes a hydrostatic gradient from said second chamber to said first chamber, whereby said media in said second chamber is held at a higher fluid level than said first chamber (when placed in a horizontal position). Adhesive and cohesive liquid forces hold said media at a higher level in said zero headspace second chamber. Consequently, a hydrostatic gradient is formed from said second chamber, where the fluid level in a horizontal position is highest, and said first chamber where the gas bubble displaces said media at the top of that chamber. Herein disclosed as a novel cell culture environment embodied in a culture vessel characterized by a novel hydrostatic gradient from said zero headspace chamber to said gas headspace chamber.

In establishing a gas gradient, said first chamber has a gas headspace and said second chamber has zero headspace. It is commonly known in the art that the gas solubility coefficient is higher for gas than it is for liquid. Therefore, the dissolved gas gradient, augmented by cellular metabolism, favors the dissolution of bubbles in said zero headspace chamber and the re-equilibration with the gas headspace (or the transposition of the gas to non-gaseous metabolites by cellular metabolism). Continuous dissolution of undissolved gas in said second chamber, helps to remove gas bubbles in that chamber and maintain a zero headspace. Herein, disclosed as a novel means to remove gas bubbles from a zero headspace cell culture chamber by establishing a dissolution gradient from said zero headspace chamber through said partition to said first chamber having a gas headspace.

In rotating the vessel, culture media in said media chamber covers the opening in said partition both when the roller bottle is standing vertically, and when it is lying horizontally. In a horizontal position, the roller bottle containing media and cell and/or tissue are disposed to a means for horizontal rotation. Said means are known in the art. Cells and tissue constructs are suspended in said tissue culture chamber one by a combination of turbulent mixing and sedimentation, when in horizontal rotation. As the roller bottle is horizontally rotated, turbulence from said first chamber through said opening in said partition is coupled to said second chamber, and is blended with the turbulence caused by the less than 1:1 viscous coupling of the roller bottle wall with the culture media in said first and second chambers. The novel blend of turbulence facilitates three-dimensional cell and tissue growth, and enhances mass transfer. The tissue constructs are unique due to their derivation in a novel hydrodynamic culture environment. Cell culture fidelity is enhanced by adding turbulence, enhancing mass transfer esp., oxygen, and better regulating the environmental parameters. In the present invention, the novel culture environment yields tissue constructs that are of higher quality then described in the prior art. The tissue constructs are formed under a novel combination of hydrodynamic selection pressures; turbulence, shear, augmented mass transfer, suspension, narrower environmental extremes and pulsatile mass transfer when cells pass by said opening through said partition.

In preventing tissue constructs from moving between said first and second chambers, velocity vectors are imposed on said constructs that alleviate movements through said opening in said partition. When the culture vessel is in the vertical position, cells sediment to the bottom i.e., said enclosed end of said second chamber, and away from said opening in said partition. In horizontal rotation, the major velocity vectors for said suspended constructs are towards earth. Hence, the movement of suspended constructs is tangential to said opening in said partition. Tangential movement without velocity vectors in the direction of the annular axis creates a barrier to entry without the use of potentially destructive mechanical or physical barriers. Herein, disclosed as a novel means to constrain the movement of cells and tissue constructs.

In rotating the tissue constructs, the roller bottle and means to retain media (e.g.; cap) are disposed to a horizontally rotating drive means. Drive means are known in the art and are available commercially, listed in many catalogs. Rotating speeds can range from 0 to 50 RPM and are determined by an operator with ordinary skill in the art, and are based on the degree of aggregation and turbulence required for the particular experiment.

In generating hydrodynamic turbulence and shear, both first and second chambers are contiguous through an opening in the partition. On one side of said partition, in said first chamber, there is a combination of gas and culture media. On the other side of said partition, in said second chamber, there is media containing cells or tissue with zero headspace. Novel hydrodynamics are created in the culture roller bottle by breaking the solid body rotation of said second culture chamber through the coupling with the turbulence from gas/media rotation in said first chamber. Hence, said second chamber loses the 1:1 viscous coupling, therein generating wall turbulence. Turbulence is generated by viscous slip at the wall-media interface. Turbulent eddies resulting from the viscous slip in said second chamber, impart shear to the growing tissue. It is known in the art that shear leads to increased mass transfer. Both shear and increased mass transfer facilitates cellular differentiation. The present inventions discloses novel hydrodynamics that uniquely blends both shear and increased in mass transfer. The combination improves the fidelity of the growing tissue construct and enables unique phenotypes.

In oxygenating the media and tissue construct, cell growth is maintained at a distance from the gas-media interface. At the gas-media interface, oxygen levels are often higher than those observed in vivo. Oxygen and other nutrients are exchanged at said opening in said partition, away from the gas-liquid interface, therein limiting oxygen toxicity. As the tissue constructs sediment, they pass through areas of high and lower oxygen tension, and nutrient concentration. Discontinuous oxygenation combined with the novel hydrodynamics of this invention yields novel tissue constructs especially suited to transplantation. Cell sedimentation through areas in the media containing high dissolved oxygen and low dissolved oxygen result in pulsatile exposure, a modeling of normal in vivo hemodynamic mass transfer. In augmenting mass transfer, turbulence and shear are constituents of the novel hydrodynamic tissue culture environment. Both turbulence and shear augment mass transfer. In mammalian cells, oxygen is the rate limiting step. Enhanced gas mass transfer from turbulence and shear, support the engineering of higher density tissue constructs. Tissue constructs are exposed to high mass transfer at two locations in the tissue culture chamber; at the media-wall interface where fluid streamlines are turbulent, and during suspension when tangentially passing said opening in said partition. Hence, tissue constructs growing in the novel hydrodynamic environment of this invention, pass through regions of high mass transfer followed by regions of lower mass transfer. Periods of high mass transfer followed by periods of lower mass transfer is a rudimentary simulation of in vivo hemodynamic systole followed by diastole. In vivo, during systole there is high mass transfer followed by diastole where mass transfer is lower.

In preconditioning islets to lower oxygen tension, the oxygen in the culture environment is regulated at a level found in the transplantation site. In contrast to naturally growing tissue having an internal blood supply, tissue for transplantation must obtain nutrients by diffusion from the outside of the construct to the interior. Most in vitro derived tissue transplants fail due to an inadequate blood supply. The present invention is useful for preconditions tissue constructs to lower dissolved oxygen levels. This invention teaches control and regulation of the dissolved oxygen culture environment in parallel with the engineering of 3-dimensional tissue constructs. Tissue constructs can be proliferated and differentiated in a low oxygen tension environment. Reduced oxygen tension goals are based on the calculated oxygen tension that the tissue construct is expected to be exposed to in the transplantation site.

In an embodiment for pancreatic islets, encapsulated for transplantation: It is not generally known that isolated islets are hypoxic, using any isolation technique. Standard insulin staining of the isolate often demonstrates a cherry red population that is inferred to be a fully functional population (together with viability stains). However, the hypoxic insult of isolation triggers apoptosis resulting in programmed cell death, and core necrosis. In vivo, the islet is highly vascularized often having a capillary vascular supply devoted to each islet. Isolation of that islet severs the vascular supply leading to hypoxia. It has been incorrectly assumed that by suspending the islet isolate in oxygenated cell culture media, oxygenation would be fully restored. The peripheral cells (on islets larger than $150\mu$ diameter) impose a diffusive gas mass transfer barrier that lowers the mass transfer rate to below $5 \times 10^{-12}$ gms $O_2$ per cell per hour. Encapsulating the islets imposes a second oxygen diffusivity barrier. The encapsulating material reduces perfusion over the cell membrane surfaces, thereby reducing the diffusivity constant to near passive diffusivity levels—a function of thickness, and pore size and porosity. Consequently, boundary conditions are established at the capsule surface (as opposed to the cell membrane surface), resulting in a zone of oxygen depletion that surrounds the islet. Additionally, cells in the hypoxia induced apoptotic or necrotic core eventually die, resulting in the release of autolytic enzymes. Autolytic enzymes concentrate in the capsule, further degrading viability. Foreign antigens are released by cell death. They contribute to the foreign antigen pool that provokes a immunological response by the host to the encapsulated transplant. The net result is generally a 90% reduction in function within a few weeks after the transplant. The instant invention preconditions developing islet constructs to low oxygen therein reducing cellular death, increasing transplantation viability, and reduces the release of cellular antigens that can induce cytokine release which can provoke an inflammatory response.

In aseptically monitoring the cell and tissue culture environment, sensors are positioned in said second chamber in contact with said culture media. Said sensors have properties, whereby their fluorescent intensity and/or color changes in response to an analyte in said culture media. Said properties include a dye embedded in a polymeric matrix or attached to a surface and having a fluorometric and/or calorimetric change in response to an analyte. Fluorescent changes and/or colorimetric changes and the analyte that they respond to, are known in the art. Said fluorescent/ colorimetric change, in response to said change in an analyte in said media, can be monitored optically. There are advantages to embedding said dye in said sensor and disposing said sensor on said roller bottle wall in contact with said media. The first advantage is, by depositing a controlled amount of sensor material on to said wall of said roller bottle, the concentration of said dye in said sensor is known. Knowing said dye concentration is important in determining the concentration of an analyte in said media i.e., the fluorometric/colorimetric change is proportional to the dye and analyte concentration. A second advantage is that said fluorometric/colorimetric changes can be monitored externally through said wall of said roller bottle. Such monitoring device incorporates an LED, or laser diode, to interrogate the sensor through the vessel wall, two photodiodes to monitor LED output and sensor absorption, a 16 bit analog-to-digital converter for each photodiode, and a microcontroller to synchronously modulate and demodulate the signal to remove background noise and synchronize sensing with rotation. The microcontroller regulates the electromagnet control of the control rod that occludes or allows mixing through said opening in said partition, therein providing environmental regulation e.g., pH and oxygen. Hence, changes in said sensor can be monitored and controlled externally, therefore the roller bottle sterility need not be breached. In the preferred embodiment, said sensor is disposed to said wall of said roller bottle during manufacturing, and said sensor is sensitive to pH or dissolved oxygen. The instant invention herein disclosed embodies a significant improvement in cost, reliability and sterility, as will be recognized by those skilled in the art.

In monitoring and regulating the culture environment, information on a particular analyte is gather from said external monitors, interrogating said internal sensors for fluorometric and/or colorimetric changes resulting from changes in said analyte concentration. Information from said interrogation is utilized to control the mixing between said first and second chambers. Said control of said mixing is accomplished by a control rod that occludes or does not occlude said opening in said partition. Said control rod is constructed of a polymeric material and is disposed in said first chamber. Said control rod further includes a north-south magnet encased in said polymeric material previously listed and having said north-south poles coaxially orientated with said annular axis of said roller bottle. Suitable magnets are commercially available and know in the art. An electromagnet is positioned external to said roller bottle, juxtaposition to said means to retain fluid, and having poles coaxially aligned with said annular axis. In controlling occlusion, said electromagnet is energized, having said pole juxtaposition to said means for retaining fluid. Energizing said electromagnet with one polarity generates a magnetic field that is the same polarity as the nearest pole of said magnet in said control rod. Generating a similar magnetic field to said nearest pole of said control rod, magnetically repels said control rod away from said means to retain fluid and into a position that occludes said opening in said partition. Conversely, reversing said electromagnetic field draws said pole of said control rod away from said opening in said partition, wherein mixing occurs between said first and second chambers. It will be appreciated by those skilled in the art that the invention herein disclosed is low cost and does not breach sterility. Moreover, the instant invention enables better control of the cell and tissue environment for better engineering of tissue constructs. Said improved control is used to tailor the engineering of novel tissue constructs.

In achieving validation, proliferating constructs must be monitored and documented. Food and Drug Administration (FDA) validation and lot release of tissue constructs, mandates numerous test of the tissue constructs for sterility, reproducibility, and fidelity. Monitoring and controlling said cell and tissue culture environment alleviates batch testing and replaces post hoc analysis with real time data. For example; once a growth profile for a tissue construct is established, the rate and time of change for the monitored parameters (e.g., pH, oxygen, $CO_2$, lactic acid, glutamine, ammonia, urea, nitrogen, glycosylation linkages—all potential analytes to be monitored by said sensors) define the growth and development of the required tissue construct. Deviations from the normal profile indicate aberrancy. Aberrance can translate into loss of sterility, reproducibility, and/or fidelity. Matching the normal profile can be used as validation method to fulfill the FDA lot release requirements. It will be appreciated by those skilled in the art, that real time validation substantially reduces tissue engineering costs, and environmental control enhances the reproducibility.

The present invention discloses a novel fluid dynamic environment embodied in a tissue culture roller bottle with two chambers, processes for engineering unique 2-dimensional and 3-dimensional tissue constructs, and uniquely segregated cell constituents of a three-dimensional tissue construct i.e., segregated by novel hydrodynamic selection pressures and environmental control. Enhanced gas mass transfer supports the maintenance of higher density tissue constructs. Monitoring and control automates the culture process and improves fidelity while lowering costs. It will be appreciated that the tissue culture roller bottle is simple to construct, very low cost, can be widely used by existing laboratories with conventional equipment, and is suited to autologous tissue culture.

DESCRIPTION OF THE PREFERRED EMBODIMENT

Figure 1:
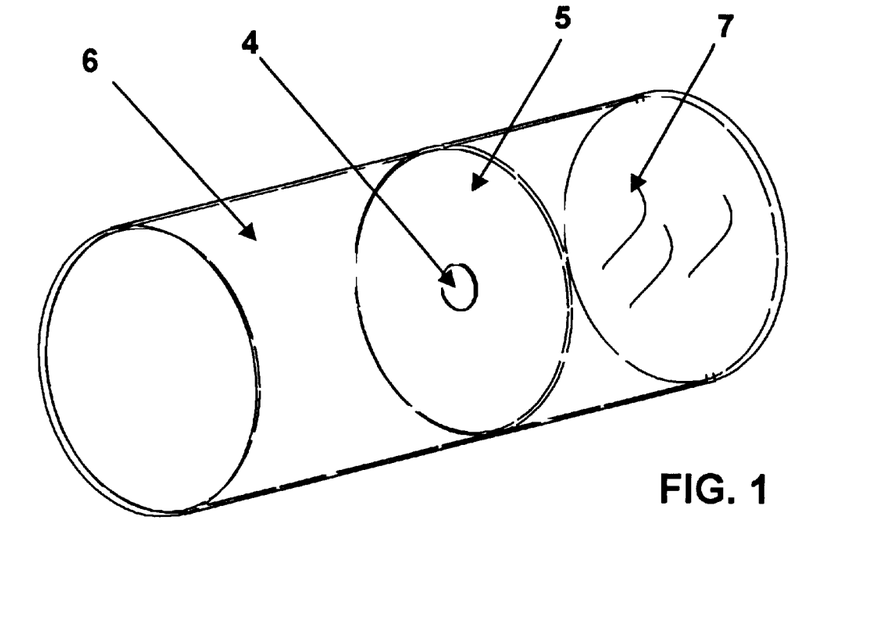
FIG. 1 is a perspective view of the culture roller bottle illustrating the two chambers.

Referring now to FIG. 1, where the perspective view shows the general organization of the present invention. The tissue culture roller bottle is divided by a partition 5 into two chambers; a first chamber 6 for culture media, and a second chamber 7 for a mixture of culture media and cells and/or tissue. The media chamber 6 and the tissue culture chamber 7 are contiguous through an opening 4 in the partition 5. The roller bottle is constructed of a polymer suitable for tissue culture.

Figure 2:
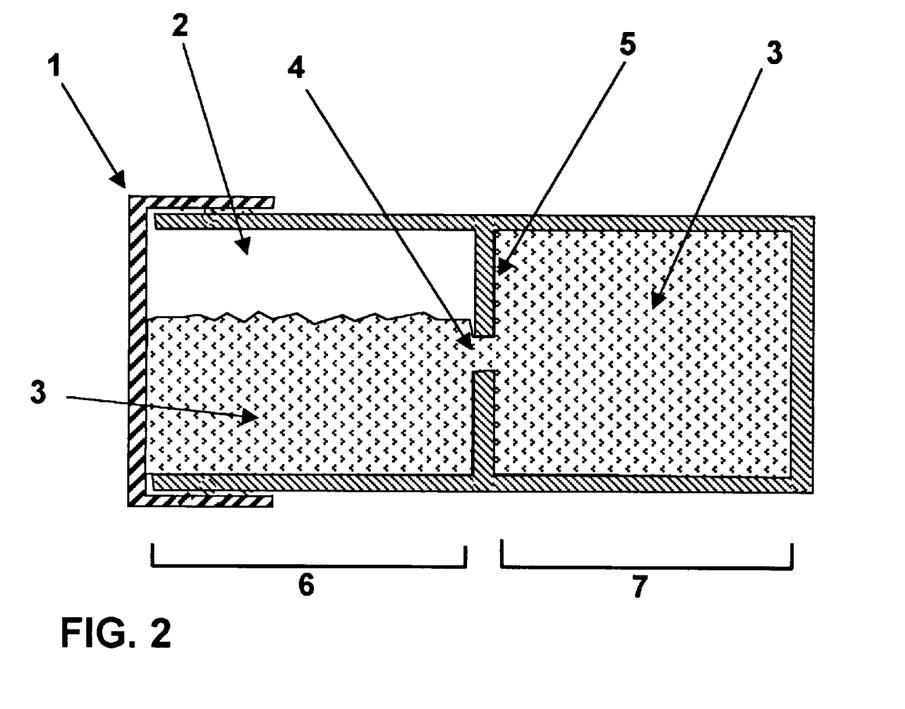
FIG. 2 is a schematized cross sectional view of the culture roller bottle containing media retained by a cap.

Referring now to FIG. 2, where the general organization of the present invention is schematized. A means to retain culture media, e.g., conventional cap 1, is disposed to said first end of said tissue culture roller bottle. Culture media 3 is present in said media chamber 6 and in said tissue culture chamber 7. The gas bubble 2 in said media chamber 6 floats to the highest point in media chamber 6 and above said opening 4 in said partition 5. Media 3 between said two chambers is contiguous through said opening 4 in said partition 5, and covers up said opening 4 in said partition 5. Therefore, said gas bubble 2 in said media chamber 6 is prevented from entering said tissue culture chamber 7.

Figure 3:
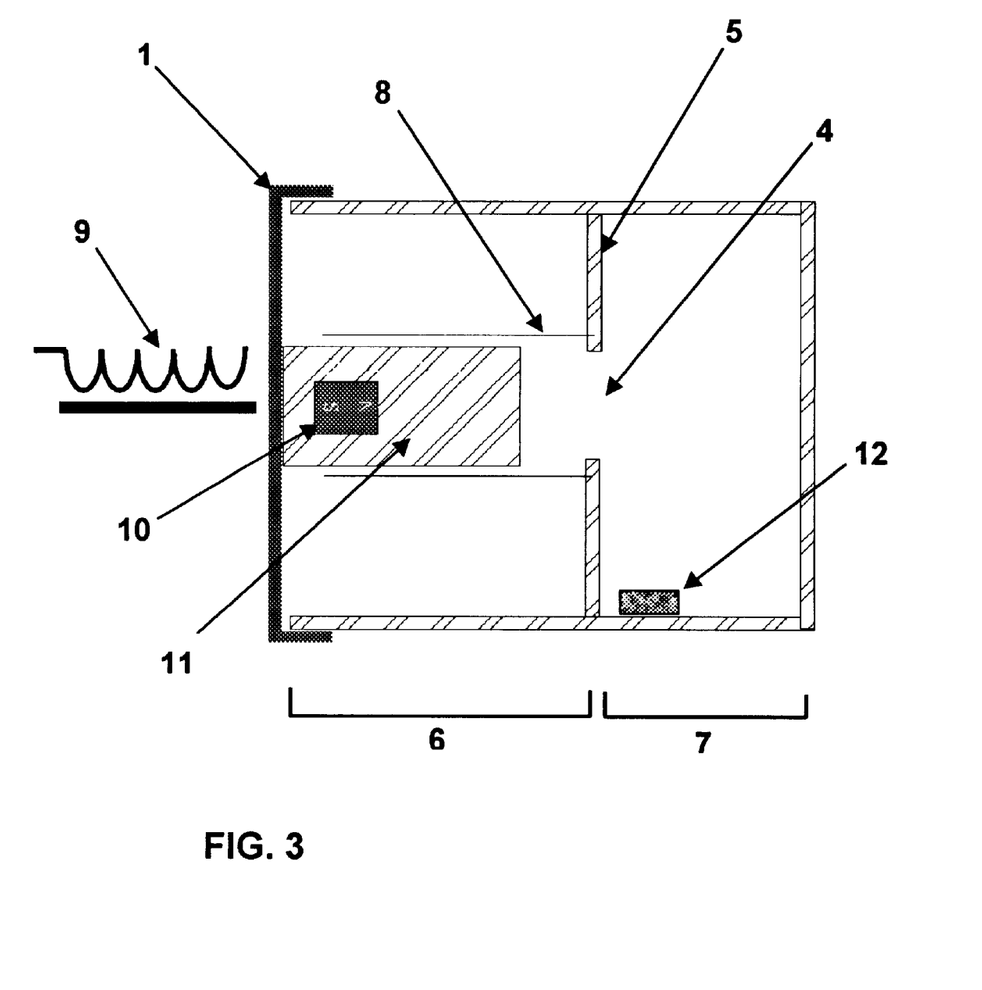
FIG. 3 is a schematized cross sectional view of the culture roller bottle depicting a control rod, an external electromagnet, and a sensor dye/matrix.

Referring now to FIG. 3, where the general organization of the automated version of the present invention is schematized. A means to retain culture media, e.g., conventional cap 1, is disposed to said first end of said tissue culture roller bottle. In said media chamber 6 there is a control rod 11 constructed of a polymer suitable for tissue culture. Encased in said control rod 11 is a north south magnet 10. Said controller rod 11 with its encased magnet 10 is mechanically constrained to the central annular axis of said roller bottle. Said constraints can be but are not limited to, posts or other mechanical means 8 deposed to said partition 5 or said control rod 11. Alternatively, said control rod 11 with said magnet encased 10, can be held by independent mechanical means. Said mechanical means 8 for constraining said control rod 11 are constructed of polymers suitable for tissue culture. When said electromagnet 9 is energized, said control rod 11 is repelled or attracted to said electromagnet because of said encased north south magnet 10. Said electromagnet 9 is located outside of said roller bottle. One polarity will cause said electromagnet 6 to repel said control rod 11, the opposite polarity will result in attracting said control rod 11. Repelling said control rod 11 occludes said opening 4 in said partition 5. Electromagnetic attraction of said control rod 11 opens said port 4 in said partition 5. External electromagnetic control 9 of said internal control rod 11 achieves several advantages: Sterility is not breached during the controlling actions, movement is externally regulated, said motion of said control rod 11 imparts turbulence and directs the turbulence, mixing between said two chambers is regulated, and the regulation of the mixing between said two chambers 6 and 7 can be based on said sensor data 12 obtained in said culture chamber 7. Said sensor 12 is disposed to said wall of said culture chamber 7. Maintained in said sensor 12 are dyes or other suitable indicators know in the art for detecting constituents in said culture media. Indicator dyes can be calorimetric or fluorescent, for example phenol red and ruthenium diimine complexes. In particular, the ruthenium diimine complexes can be chosen from tris-2,2'-bipyridyl ruthenium (II) salts, including the chloride hexahydrate salt, tris-4,7-diphenyl-1,10-phenanthroline ruthenium (II) salts, including the chloride salt, and 9,10-diphenyl anthracene. To detect the changes in said sensor 12, a detector suitable for said particular sensor is located externally. It will be appreciated by those of ordinary skill in the art that said culture roller bottle with sensor 12 and control rod 11 are simple to construct, low cost, and disposable. Moreover, a variety of features are integrated into a single unique disposable roller bottle.

As an example of use of said cell culture system, Ham's F10 media can be sterilized and placed into said cell culture chamber. Said tissue culture chamber is completely filled with cells and/or tissue and media. Cells are commercially available, derived from cell lines, derived from animals, or obtained from human donors. Herein, cells shall refer to cells, tissue or a mixture of cells and tissue. Said media chamber is then filled to $\frac{2}{3}$ its volume with culture media, the remaining $\frac{1}{3}$ volume is gas. Chamber volumes can range from less that 1 ml to several litters. To provide the necessary ambient environment, said culture roller bottle is placed into a conventional incubator where it rotates, and turbulence, pulsatile mass transfer and shear provide for proliferation and monolayer and/or three-dimensional growth.

Cells are suspended by adjusting the rotating speed. Suspension is observed when there is a balance between sedimenting and turbulent forces. In the present invention, mammalian and animal cells will grow and aggregate in suspension. Cellular aggregates can range from 50 microns to several cm. As the cells aggregate, they form an autologous extracellular matrix upon which cells adhere, differentiate and become 3-dimensional tissue. Tissue constructs developed in the novel hydrodynamic environment of this invention are unique. Turbulence, pulsatile mass transfer, and shear place unique selection pressures upon the growing construct. Cells that are robust to turbulence and shear, thrive on the outside of the construct where the exposure is the greatest. Those cell subpopulations that require lower oxygen tension thrive in the core of the construct. Consequently, selection and segregation based on the novel culture and hydrodynamic environment leads to the growth and differentiation of tissue constructs that are unique to the two-chamber culture environment of this invention.

The present invention improves the gas mass transfer to the culture media, and eliminates the toxic silicone membrane oxygenator that is in general use in the art. Gas in said media chamber is in direct contact with culture media. As said roller bottle rotates, the gas in said media chamber is directly mixed with culture media. Rotation disrupts the gas-media boundary layers, facilitating gas mass transfer. Media adherent to said wall and drips off the walls during rotation, further augmenting gas mass transfer. Elimination of the silicone membrane (or any other oxygenation material) oxygenator removes the major impediment to gas mass transfer. Moreover, silicone has been implicated as a potential disease causing agent. It is known in the art that during periods of cellular proliferation and differentiation, cell are especially susceptible damaging agents. Engineering tissue constructs requires cellular proliferation and differentiation.

The present invention mitigates the loss of cells during feeding. Examples of culture vessels that lose cells during media replacement are: t-flasks, petri dishes, roller bottles, stirred vessels, and horizontally rotating vessels. In the present invention, while in vertical position, cell sediment to the bottom of the tissue culture chamber. Media is siphoned from the surface without disturbing the sedimented cells. In contrast to t-flasks and rotating vessels, where the vessel is place on end and non-adherent cells are lost when the media is removed. In horizontal rotation of the present invention, cell movement is tangential to the opening in the partition. Consequently, cells fall past the opening. The velocity vectors direct cellular movement past the opening thereby restricting their entrance into the media chamber. To replace media in the media chamber, the vessel it tilted to a vertical position wherein the cells sediment to the bottom of the tissue culture chamber and away from the media chamber. Thus, substantially all the cells are retained during media repletion/replacement. Following media repletion, the vessel is gently tipped back to a horizontal position and rotated. During rotation the cell movement vectors again become tangential to the opening in the partition. It will be appreciated by those of ordinary skill in the art, that media exchange at the opening in the partition without cellular loss to the media chamber, is an instant invention. Furthermore, the tissue constructs are unique because they are engineered from cell subpopulations that are typically lost during conventional media repletion. The lost subpopulation includes stem cells. The aggregation of cells that are typically lost during media repletion with cells that are generally present after media repletion, yields unique tissue constructs. The unique constructs have phenotypes that differ from constructs cultured in other vessels.

EXAMPLE 1

A tissue culture roller bottle of this invention, injection molded with cell culture grade polystyrene (e.g., Wheaton Science Products, Millville, N.J.), was sterilized by methods know in the art. The roller bottle was placed in a vertical position. A mixture of culture media and cells was added until the culture chamber was completely filled. Cell concentrations ranged from $10^5$ cells/ml to $10^7$, and were normal human epidermal keratinocytes. Other cells in the co-culture included; fibroblasts, melanocytes, and epidermal stem cells. Fresh culture media was utilized to fill ⅔ of the remaining volume of the media chamber. The last ⅓ volume of the media chamber was left empty i.e., gas filled the remaining ⅓ media chamber volume. The cap was disposed to the first opening and the culture roller bottle was slowly tilted to a horizontal position. In moving the culture roller bottle from a vertical position, the gas trapped in the media chamber moved to the highest point in the media chamber. The media volume was chosen so that when the roller bottle was positioned horizontally, the culture media covered the opening in the partition, preventing the gas bubble from entering the tissue culture chamber. The culture roller bottle was disposed to a means to rotate, cell culture rotators are know in the art and can be purchased (e.g. Fisher Scientific, Tex.). The culture roller bottle disposed to a rotator was placed in a tissue culture incubator at 37° C. Rotation was started at approximately 20 rpm. Small cell aggregates formed within a few hours and larger aggregates gradually develop thereafter. Microcarrier beads may be included for attachment and support, or the tissue culture chamber walls may be specially modified to encourage tissue attachment. Microcarrier beads with densities less than the cell culture media, can be utilized for attachment, and to constrain tissue constructs to the area surround the annular axis and away from the cylinder wall.

Constructs remain undisturbed in culture for longer periods of time, as compared to conventional culture. The extended culture duration is due to the additional media contained in the media chamber. Mixing between the media chamber and the tissue culture chamber is slow. Slowly mixing fresh media from the media chamber, with the tissue culture chamber, effectively prolongs the undisturbed culture time. Standard culture practice is to re-feed cultures by replacing 50–100% of the depleted media with fresh media. A consequence of that approach, is that de novo growth factors are abruptly removed, harming the proliferating constructs. In the present invention, the rate of media repletion (growth factor reduction) is substantially reduced; and growth factor concentration remained higher throughout the culture process.

The process of choosing a cell type(s) and proliferating the cells into 3-dimensional aggregates, constitutes tissue engineering. Cellular aggregates derived from the present invention have broad utility, and special utility in autologous transplantation because of the ability to pre-conditioning explants. The novel combination of hydrodynamic forces and augmented mass transfer is suited to the growth of autologous tissue constructs and unique tissue constructs. Sizes and shapes vary and can take the form of cellular aggregates or, sheets of cellular and extracellular material. The present invention can be used to expand a population of normal human cells or stem cells into a larger population. That expanded cell population would be useful for transplantation back to the original host or to a different tissue compatible host. Additionally, the engineered tissue can be used for research; testing gene therapies, viral propagation, new drug treatments and/or for testing fundamental biological theory.

EXAMPLE 2

In an alternate embodiment for the manufacturing of the culture roller bottle, the media chamber and partition with opening were injected molded or vacuformed as a separate chamber member. The media chamber was inserted into the culture roller bottle member. The first media chamber member defined the media chamber, the volume between the partition and the second of the cylinder member defined the tissue culture chamber.

EXAMPLE 3

In an alternate embodiment for automating media repletion, the control rod member incorporated six leg members that extended from and perpendicular to the annular axis. The leg members mechanically constrained the control rod in the media chamber but allowed free mobility along the annular axis within the media chamber. The control rod member was centered in the annular axis of the cylinder. Encased in the control rod, was a north/south magnet, also aligned with the annular axis of the cylinder. External to the culture roller bottle was a conventional electromagnet or other means for generating a magnetic field. The preferred location was near the cap. When the electromagnet was energized and generated a magnetic field opposite that of the nearest pole in the control rod, the control rod was pulled toward the cap and away from the opening in the partition. When the electromagnet polarization was reversed, the nearest pole in the control rod was repelled, pushing the control rod away from the cap toward the opening in the partition. Thus, the control rod was externally repelled or attracted to occlude or open the opening in the partition, respectively. External control rod activation eliminated the risks of contamination. The cells in the culture chamber can be fed by engaging the electromagnetic to pull the control rod away from the opening in the partition, allowing mixing between the two chambers. Alternatively, early in the tissue construct development, the control rod is be pushed to occlude the opening and minimize mixing. Minimizing mixing would allow de novo growth factors to increase in concentration at a time when the tissue construct needs the highest concentration of growth factors.

EXAMPLE 4

In an alternate embodiment for automating media repletion, a dye incorporated into a matrix was placed in the tissue culture chamber that was sensitive to one or more environmental parameters. Said dye can be in solution or immobilized. As example, but limited to, phenol red (Sigma, St. Louis, Mo.) covalently bound to a matrix was utilized to monitor pH. A second example was ruthenium diimine complex (Sigma, St. Louis, Mo.) which was utilized to monitor dissolved oxygen. An external monitor that included an LED, photodiodes and a microcontroller, interrogated the dye/matrix to determine the absorbance change (phenol red) or fluorescent change (ruthenium diimine). Based on the calorimetric (or fluorometric) changes of the indicator dye, the electromagnet was energized to move the control rod and occlude the opening, or allow the media and tissue chambers to mix. External monitoring and control eliminated contamination risks. The entire culture roller bottle, control rod and indicator dye was disposable. A disposable automated tissue culture unit is especially suited to autologous tissue culture and suited to meeting federal regulatory requirements.

It can be appreciated that the maintenance of a normal metabolic environment, through enhanced gas mass transfer and automation in the present invention, would improve the scientific capability for engineering tissues. Costs and FDA compliance are significantly improved by using a disposable culture roller bottle and standard rotating devices.

EXAMPLE 5

In an alternate embodiment for engineering sheets of tissue, normal human epidermal keratinocytes (Clonetics, Calif.) were placed in the tissue culture chamber with media (Clonetics, San Diego, Calif.). This method and product-by-process is suitable for cartilage constructs. The roller bottle was placed in a vertical position. The keratinocytes and other cells associated with the epidermal layer, were allowed to sediment to the bottom and attach to the wall opposite and parallel to the partition. After 4–7 days, depending on initial seeding densities, cells were 90% confluent. The roller bottle was then placed in a horizontal position and rotated, as previously described. Non-adherent cells were suspended in the tissue culture chamber by horizontal rotation. Suspended cells differentiated and adhered to the 90% confluent monolayer resulting in a sheet of tissue. The thickness of the developing sheet of tissue was governed by seeding density and the time maintained in culture. It will be appreciated by those of ordinary skill in the art that a variety of shapes, thickness and tissue phenotypes can be engineered.

EXAMPLE 6

In an alternate embodiment for proliferating human hepatocytes, normal human hepatocytes were cultured and expanded. A human liver enzymatic digest substantially consisting of normal human hepatocytes was obtained from Clonetics (San Diego, Calif.). The minor cellular elements in the digest were normal cellular constituents that comprise a normal human liver. Hepatocytes were suspended in culture media (Clonetics, San Diego, Calif.), then pipetted into the tissue culture chamber. The tissue culture chamber was filled with media to have zero headspace and the media chamber was filled with the same media. An ambient gas headspace filled the remaining ⅓ of the media chamber. The roller bottle was placed in a horizontal position and rotated as previously described. Typically, hepatocytes and other cellular constituents do not aggregate. However, in the present invention 3-dimensional tissue constructs developed. The constructs were suited to clinical therapies. It will be appreciated by one of ordinary skill in the art that the ability to grow and expand normal cells into tissue constructs has a variety of applications.

EXAMPLE 7

Frozen human islets are quick thawed and placed in standard culture media and 10% FBS. Several different medias are known in the art and can include CMRL 1066 media. Islets are cultured for the first 18–24 hours in a t-flask. The initial t-flask culture, helps to remove acinar that contaminate the culture and cellular debris from cells lost due to freezing/thawing. Cellular aggregates, predominately islets >80%, are dislodged from the bottom of the t-flask by several blunt palm taps. Islets are then pelleted at 50×g for 5 minutes and 25% of the bottom volume is resuspended in the same culture media (except 5% FBS) that has been equilibrated to 80 mm Hg $dO_2$, balance $CO_2$. Islets are then placed in a 6 ml culture vessel of the present invention that is operated for 7–10 days in automated suspension mode, where environmental pH and oxygen are monitored and regulated. This step stabilizes the culture by improving the viability and allowing the cells that were in early apoptosis, as a result of pancreatic isolation procedures, to complete the programmed cell death and wash away. The 6 ml islet suspension is expected to be >95% viable by day 7–10. After the first 7–10 days, the vessel is switched to static mode for 5–9 days, where the culture vessel is in a non-rotating vertical position. In static culture, islets will become disaggregated. This appears to the most gentle method for islet disaggragation. The vessel is then switched back to suspension mode, allowing the individual disaggregated cells to form cellular nucleation sites. Each nucleation site will both adhere to other cells that have a contact predilection for that subpopulation and, aggregate constituents will replicate/ differentiate into 3-dimensional islet constructs. The first month is a fragile development period in any suspension culture. During the first month, extracellular formation is susceptible to disaggragation. Consequently, during the first month the 150µ diameter monitoring is by observation only.

After the first month of culture, aggregates are more robust and better tolerate vessel handling. From month 2–3 the serum concentration is reduced from 5% to 2%. In this invention, once a construct has developed a stable autologous extracellular matrix, there is less of a need for serum and other growth factors. Furthermore, serum reduction measures will reduce costs and lessen the FDA screening requirements. Occasional representative samples are drawn with large bore pipette tips—small volumes so as not to deplete the developing culture. The number of cells in an islet aggregate is variable. Standard hemocytometer and coulter counter methods are accepted standards. In an alternate embodiment, the vessel will be monitored for biomass increases and aggregate size distribution, by laser light scatter. Briefly, as the density and size of the cellular aggregates change, the frequency of the laser beam disruption changes; as the vessel rotates through a laser beam that has been transformed to a line. Fast Fourier Transfer of the time domain data, collected from light scattering off the cellular aggregates, provides density and size distribution data that can be normalized to the first and last calibration samples. Integrating the intensity and size distribution data is proportional to the biomass.

Samples taken from the 2–3 month maturation period are DTZ stained. It is anticipate that early during the maturation phase that DTZ staining will be very weak. Later, at the end of the maturation phase, islet constructs will be a pale pink. DTZ staining is better correlated with mature insulin packaging than extracellular insulin levels or islet function. After three months, representative samples are collected and tested for function. Islet construct functions are assessed by static glucose stimulation (SGS). Briefly, 100 islet equivalent (IEQ) islet constructs (define as 150µ diameter islet construct) are washed and incubated in 50 mg % glucose for baseline determination. After baseline assessment, the same 100 IEQs are incubated in 300 mg % glucose with 10 mM theophylline and spent media collected. The same batch is washed with 50 mg % glucose media and incubated in the baseline media, to obtain return to baseline measurements. Assuming return to baseline, a 2× insulin production over baseline is the minimum acceptance criteria for mature islet constructs. Alternately, islets derived from fetal or adult donors are utilized to create immature 150µ constructs. The 150µ constructs are transplanted into the host, maturing in the host to functional constructs.

Once aggregation occurs, oxygen preconditioning begins. Early in the process oxygen tension is high to compensate for the loss of the vascular supply—when the islets were removed from the pancreas. As cell constituents of the islet re-aggregate to form a new islet construct, a preselection process begins. The new islet constructs become functional without a vascular supply. Over a 10–40 day period, the oxygen tensions are lowered to oxygen tensions expected to be found in the transplantation site. For unencapsulated islets, final oxygen tensions are approximately 60 mm Hg. For encapsulated islets, oxygen tensions are 40–50 mm Hg. Both pH and oxygen are controlled, to maintain low oxygen tension concurrently with a physiological culture environment Islet encapsulation has been previously described. Islet constructs are washed once in calcium and magnesium free HBSS. The islets in HBSS are co-axially extruded with 1.5% alginate into a 0.5 cm 28 gauge tube for droplet generation. This reduces the alginate exposure time. The final alginate concentration is approximate 1% after co-extrusion. Alginate/islet drops, 1:1 islet/capsule, are generated into cell culture media with 5% FBS. The media with serum has sufficient free calcium to solidify droplets and enough protein to saturate alginate partitioning.

In an alternate embodiment, islet aggregates are co-cultured with mammalian sertoli cells, resulting in sertoli/islet aggregates. The sertoli/islet constructs would be less immunogenic than other allogeneic or xenogeneic constructs. It is known in the art that sertoli cell produce FasL, an immunosuppressant factor. The construct is transplanted under the kidney capsule, or in an alternate embodiment, encapsulated and transplanted to the abdominal peritoneum.

EXAMPLE 8

In fertilizing and developing embryos, mammalian eggs and sperm are pipetted into the tissue culture chamber filled to a zero headspace with culture media suitable for fertilization and growth. The media chamber is filled with culture media to have a gas headspace as previously described. The vessel is tilted from a vertical position to a horizontal position and disposed to a means to horizontally rotate the vessel. Environmental oxygen and pH are monitored and controlled as previously described. Sperm bind to the eggs, penetrate and fertilize the eggs. Fertilized eggs in suspension undergo maturation, forming moruli, early blastocyts, then trophoblasts (when co-cultured). In addition to facilitating fertilization and maturation, this invention enables the growth of embryonic tissue free from immunological surveillance. It will be appreciated by those of ordinary skill in the art that this method and product-by-process has a variety of applications. Alternatively, endometrial tissue is co-cultured with the fertilized egg, later forming endometrial implantation constructs that support embryonic maturation. The endometrial elements will eventually form decidua with phenotypic and morphological attributes that characterize implantation. The process will continue until the construct becomes mass transfer limited and requires transplantation to a receptive uterus. It will be appreciated by those of ordinary skill in the art that the present invention mitigates the loss of eggs, sperm, and co-culture cell during the feeding. In a clinical in vitro fertilization setting, the loss of an egg could be catastrophic.

EXAMPLE 9

In proliferating cardiac myocytes, human cardiac myocytes with the cell constituents that support the primary architecture are obtained from Clonetics (San Diego, Calif.). The myocytes are washed in media (Clonetics, San Diego, Calif.), pelleted at 50×g and placed in the culture chamber. The culture chamber is filled to zero headspace with media, and the media chamber is ⅔ filled with media and ⅓ filled with ambient air. A cell monolayer will begin form at the bottom of the tissue culture chamber in 4–7 days. After an initial monolayer has formed, the vessel is tilted to a horizontal position and rotated. Rotation suspends the growing myocyte constructs while the wall monolayer serves as a feeder layer, providing growth factors and other support. Once the myocyte population is expanded to a biomass suitable for transplantation, the media is removed and constructs pelleted and washed in normal saline. Proliferated myocytes are injected into the site of myocardial damage. In an alternative embodiment, myocytes are selected from the group consisting of cardiac, skeletal, myocyte stem cells, and smooth muscle, and utilized for treatment of their origin. For example, proliferated skeletal muscle cells can be transplanted into skeletal muscle to overcome various muscular dystrophies.

EXAMPLE 10

In developing therapeutics for HIV, human lymphocytes are collected from the peripheral blood and/or lymph nodes. Explants or enzymatically dissociated cells are placed in to culture chamber and both culture and media chambers are filled with media as previously described. It is known in the art that lymphocytes traffic virus between lymph nodes. Suspension in the current invention would support trafficking between explants. Virus infected explants or native virus is placed in the culture chamber. Drugs are screened for activity by adding the drug, or combination of drugs, to the media at various stages in the inoculation. Samples are withdrawn and analyzed for viral load and cellular incorporation of the virus. Furthermore, the control rod can be used to regulate the timing and the amount of drug or virus that enters the culture chamber. Therapeutics or virus being placed in the media chamber and added to the culture chamber by controlling the occlusion of the opening in the partition.

EXAMPLE 11

In developing chimeric constructs, human cells and foreign human or non-human cells are co-cultured as previously described for normal tissues. The co-culture achieves a level of function that has a therapeutic benefit. In one of many instances know in the art, tissue macrophages are harmful to the developing construct. They can react to aberrant phenotypes or cellular metabolism, releasing cytokines and other products therein eliciting an inflammatory cascade. Inflammation can result in the rejection of a transplanted construct. Co-culturing of human islets or neuronal cells with similar cell types from an allogeneic or xenogeneic donor can activate both sets of tissue macrophages. Activation will eventually deplete the activated subpopulation, resulting in a surviving population substantially free from tissue macrophages.

EXAMPLE 12

In propagating virus, cellular constructs are cultured and matched with the virus that is know to grow in that cellular host. The predilection of certain viruses for specific tissues is known in the art, or specific gene therapies disposed to viral based vectors are utilized for gene therapy. The present invention facilitates the growth of both monolayer and 3-dimensional tissue constructs, and mitigates the depletion of non-adherent cell phenotypes lost during feeding, resulting in a plethora of phenotypes that are not typically present in culture. Hence, tissue constructs are engineered to have autologous extracellular matrix, architecture, and phenotypes that are conducive to viral propagation. For example, mesenchymal cells obtain from human donor proximal intestinal tissue (or neuronal cells for neurotrophic viruses) are placed in the tissue culture chamber as previously described. The cells are cultured for 10–14 days to allow for adaptation, autologous extracellular matrix formation, and for the expression of phenotypes that are unique to the novel culture vessel and environment of this invention. After 10–14 days, 10 $\mu$l of virus obtained from Centers for Disease Control is add to the tissue culture chamber. Following two viral doubling periods, samples are collected and analyzed for intracellular virus and free virus. Lytic viruses that tend to deplete standard cultures of their cellular host, will continue to propagate for longer periods due to the cellular regenerative capacity implicit in the tissue constructs of this novel culture vessel and environment.

In an alternate embodiment, the viral vector contains specific sequences for the production of recombinant protein. In the present invention, a greater level of recombinant production is achieved, owing the improvement to the regenerative capacity of the growing constructs.

In an alternate embodiment, viral vectors include knock-out sequences for incorporation into the genome. Cellular knock-outs proliferate in the present invention can be utilized in basic research and transplantation.

EXAMPLE 13

In propagating bone marrow, neonatal cord blood or bone marrow collections are cultured in the tissue culture chamber. The stem cells from the cord blood or bone marrow along with the more mature cell constituents, are cultured in suitable media as a monolayer for 2–3 days. During the first few days of monolayer culture, the cells will gently disaggregate and form a monolayer with patches of multicellular constructs. The multicellular patches and monolayer will later become the stromal feeder layer. The culture vessel is then horizontally tilted and rotated. Non-adherent stem cells will detach from the monolayer and stromal patches and become suspended. As the suspended cell proliferate and differentiate, new adherent phenotypes will develop and adhere to the feeder layer. After 30 days, enough marrow will have been propagated to seed additional vessels, and eventually, depending on the weight of the recipient, enough for transplantation.

EXAMPLE 14

In producing a validated product-by process, hyaline cartilage obtained by surgical means from the knee is enzymatically dissociated and placed in the tissue culture chamber. Cartilage is cultured as a monolayer for 2–3 days therein forming a monolayer with patches of multicellular constructs. The vessel is then rotated and pH and oxygen monitored and controlled for 22 days. Oxygen is maintained at low oxygen tension, approximately 40 mm Hg. The same process is reproduced several times to establish a typical pH and oxygen utilization profile with the required degrees of freedom to detect statistical outliers. Once a standard profile has been established, processes falling three standard deviations from the normal profile, are rejected. Aberrancies caused by atypical starting material, contamination, or quality control deficiencies, are identified and the autologous tissue lot rejected. Hence, the product-by-process is the autologous construct that matches the standard profile for oxygen and pH changes. In many instances, it is the standard of practice to qualify tissue after it has been cultured or transplanted. Real time monitoring and control of oxygen and pH changes improves safety by identify contaminated tissue or atypical tissue prior to transplantation, and improves reproducibility.

EXAMPLE 15

The sensor platform consists of: LEDs for interrogating sensor dyes or dye/matrix, a low drift photosensor subassembly (non-linearity ±0.2% F.S., supply sensitivity 0.5%/V, temp. coef. ±100 ppm/°C., 20 bits resolution), and requires 5 V @ 2 mA average), the MC68HC705P9 microcontroller, and an interface (direct, IR or USB depending on the application). Alternatively, a sampling 16-bit analog to digital converter can be used. Estimated MTBF for the platform is approximately 50,000 hours (the individual components have MTBF typically >100,000 hours). The sensor platform drifts less than 0.5% per year, consumes, on average, 10 $\mu$A power @ 5 V, peak power consumption is 20 mA @ 5 V, and can collect approximately 4,000 measurements powered from a 9 V alkaline battery. The sensor platform is a generic platform; to change from pH to $dO_2$ to glucose, only the solid matrix containing the sensing dye and the appropriate wavelength LEDs are changed, for $dO_2$ a filter is added. The matrix consists of a porous material that is sterilized and placed in the cell culture. An example of dye/matrix material includes: silicone for the ruthenium diimine complex and fibrous cellulose for the covalently coupled phenol red.

It will be apparent to those skilled in the art that various changes may be made in the invention without departing from the spirit and scope thereof, and therefore the invention is not limited by that which is disclosed in the drawings and specifications but only as indicated in the appended claims.

I claim:

1. A two chamber roller bottle providing a hydrostatic gradient between the two chambers, consisting essentially of:
    a cylinder member with an enclosed second end and a first end with a first means for introducing culture media and cells,
    said cylinder member having a partition that defines a media chamber between the partition and the first end and defines a culture chamber between the partition and the second end,
    said media and culture chambers being coaxially aligned and aligned with the annular axis of said cylinder member,
    said partition having an opening aligned with the annular axis of the cylinder member,
    said partition and opening being constructed and arranged such that when the bottle is in a vertical position, media can be introduced using the first means to completely fill the culture chamber and partially fill the media chamber and when the bottle is in a horizontal position, the introduced media completely fills the culture chamber and partially fills the media chamber, and
    means for retaining the culture media disposed to the first means for introducing culture media and cells.

2. The two chamber roller bottle of claim 1 wherein:
    a control rod is disposed in said media chamber,
    said control rod encases a north-south magnet,
    said control rod and encased magnet are aligned with the annular axis,
    said control rod and encased magnet are constrained to the media chamber,
    said control rod and encased magnet are freely movable in the annular axis, and
    an electromaget juxtaposition to said means for retaining media and outside said media chamber and aligned with the annular axis.

3. A method for allowing or restricting media exchange between said chambers of claim 2 wherein:
    said electromagnet is energized,
    said energized electromagnet repels said control rod and encased north-south magnet,
    said repelled control rod is moved to occlude said opening in said partition therein restricting media exchange between said chambers, or
    said electromagnet is energized,
    said energized electromagnet attracts said control rod and encased north-south magnet,
    said attracted control rod is moved to un-occlude said opening in said partition therein allowing media exchange between said chambers.

4. A method for culturing cells in a two chamber roller bottle comprising:
    a cylinder member with an enclosed second end and a first means for introducing culture media,
    said cylinder member having a partition that defines a media chamber and a culture chamber,
    said media and culture chambers are coaxially aligned and aligned with the annular axis of said cylinder member,
    said media chamber is defined between the first means for introducing culture media in said cylinder member and said partition,
    said culture chamber is defined between said partition and said enclosed second end of said cylinder member,
    said partition having an opening aligned with the annular axis of the cylinder,
    said culture chamber filled with culture media and cells to have a zero headspace,
    said media chamber filled with culture media to have a gas headspace,
    means for retaining the culture media disposed to the first means for introducing culture media, and
    disposed to a horizontal rotating means to culture cells.

5. A method for culturing cells in a two chamber roller bottle comprising:
    a cylinder member with an enclosed second end and a first means for introducing culture media,
    said cylinder member having a partition that defines a media chamber and a culture chamber,
    said media and culture chambers are coaxially aligned and aligned with the annular axis of said cylinder member,
    said media chamber is defined between the first means for introducing culture media in said cylinder member and said partition,
    said culture chamber is defined between said partition and said enclosed second end of said cylinder member,
    said partition having an opening aligned with the annular axis of the cylinder,
    said culture chamber filled with culture media and cells to have a zero headspace,
    said media chamber filled with culture media to have a gas headspace,
    means for retaining the culture media disposed to the first means for introducing culture media, and
    culturing cells in a suitable sequence that includes vertical stationary culture for monolayer proliferation and disposed to a horizontal rotating means for 3-dimensional culture.

* * * * *